United States Patent

Nosco et al.

Patent Number: 4,925,650
Date of Patent: May 15, 1990

[54] TECHNETIUM-99M COMPLEX FOR EXAMINING THE RENAL FUNCTION

[75] Inventors: Dennis L. Nosco, Florissant, Mo.; Alfons M. Verbruggen, Leuven, Belgium

[73] Assignee: Mallinckrodt, Inc., St. Louis County, Mo.

[21] Appl. No.: 272,177

[22] Filed: Nov. 16, 1988

[51] Int. Cl.$^5$ .................... A61K 49/02; C07F 13/00
[52] U.S. Cl. ...................................... 424/1.1; 534/14
[58] Field of Search ............................ 424/1.1; 534/14

[56] References Cited

U.S. PATENT DOCUMENTS 2,810,753 10/1957 Bersworth ...................... 424/1.1

FOREIGN PATENT DOCUMENTS 0188256 7/1986 European Pat. Off. ............ 424/1.1

OTHER PUBLICATIONS

Fritzberg, A. R. et al., "Synthesis and Biological Evaluation of TC-99m", J. Nucl Medicine, vol. 23, No. 7, 7/82, pp. 592-598.

Primary Examiner—John S. Maples
Attorney, Agent, or Firm—David A. Hay; Roy J. Klostermann

[57] ABSTRACT

The invention relates to a technetium-99m complex of the general formula

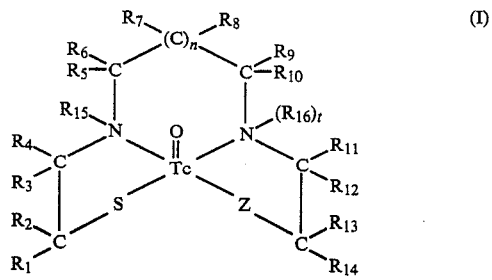

wherein Z is a sulphur atom or an amino group of the general formula $R_{17}$—N—$(R_{18})_k$, in which k is 0 or 1 and $R_{17}$ and $R_{18}$ have the same meanings as the symbols $R_1$-$R_{16}$;

each of the symbols $R_1$-$R_{16}$ is individually selected from the group consisting of hydrogen, straight or branched, unsubstituted or substituted alkyl having 1-4 carbon atoms, and ACOOH, wherein A is a straight or branched, unsubstituted or substituted alkly group having 0-4 carbon atoms;

and $R_5$ together with $R_6$ or $R_9$ together with $R_{10}$ additionally may form an oxygen atom;

Tc represents technetium-99m;

t is 0 or 1; and n is 0 or 1;

with the provisos that (a) if $R_{15}$, $R_{16}$, $R_{17}$ and/or $R_{18}$ are/is ACOOH, A is a straight or branched, unsubstituted or substituted alkyl group having 1-4 carbon atoms;

(b) at least one of the symbols $R_1$-$R_{18}$ is ACOOH; and (c) if t is 1, at least two of the symbols $R_1$-$R_{18}$ are ACOOH;

or a pharmaceutically acceptable salt of this compound.

The invention further relates to a radiopharmaceutical composition comprising said complex, to the use of this composition for examining the renal function, and to a kit for preparing such a composition.

15 Claims, No Drawings

TECHNETIUM -99M COMPLEX FOR EXAMINING THE RENAL FUNCTION

The invention relates to a technetium-99m complex and to a method of preparing said complex. The invention further relates to a radiopharmaceutical composition comprising said complex, to the use of said composition for examining the renal function, and to a kit for preparing such a composition.

Radioactive labelled compounds are used for the examination of patients, for example, into deviations in shape and function of internal organs and into the presence and location of pathological processes in the body. For this purpose, a composition in which the radioactive compound is present is administered to the patient, for example, in the form of an injectable liquid. By means of suitable detection apparatus, e.g. a gamma camera, images can be obtained of, for example, the organ or the pathological process in which the radioactive compound has been incorporated, by recording the emitted radiation. Compounds which are generally used for examining the renal function are radioactive iodo-Hippuran® and Tc99m-diethylene triamine pentaacetic acid (DTPA), which will be discussed hereinafter.

In addition to glomerular filtration, an active tubular secretion also takes place in the kidneys. The functioning of the kidneys is determined to a considerable extent by the functioning of the kidney tubules. In an adult person approximately 125 ml of blood plasma per minute is purified by glomerular filtration. This means: the clearance is 125 ml per minute. The total clearance which can be effected by the kidneys is 600 to 700 ml of plasma per minute. It appears from the clearance of 100 ml of blood plasma per minute which is found for the above-mentioned chelate of DTPA that said chelate is eliminated entirely or substantially entirely by glomerular filtration and hence is not very suitable for examining the renal function.

An example of a radioactive iodo-Hippuran® compound generally used for examining the renal function is iodo-131-Hippuran® which, as is generally known, is secreted actively tubularly and hence is very suitable for examining the renal function as regards organ specificity.

There exists a great need for a suitable composition for examining the renal function which is permanently available, in particular for kidney transplantation patients, accident victims and patients after large vascular operations.

The above-mentioned iodo-131-Hippuran® would be excellently suitable for these applications, also due to its ready availability. Like all iodo-131 compounds, iodo-131-Hippuran®, however, constitutes a serious radiation burden for the patient. Therefore, said iodo-131 compound can be administered to the patient only in restricted doses, as a result of which the resulting information is insufficient to obtain statistically reliable images of the renal function by means of a gamma camera.

Another radioactive iodo-Hippuran® compound frequently used for examining the renal function is iodo-123-Hippuran® which is excellently suitable as regards the organ specificity and the restricted radiation burden. Iodo-123-containing compositions, however, have only a restricted availability due to the short half-life, namely 13.3 hours, and because the production of iodo-123 must necessarily be carried out in a cyclotron.

Technetium-99m complexes which show a tubular secretion which is comparable to that if iodo-Hippuran® are known from European patent application 173424. This application discloses inter alia the preparation of Tc-99m-mercaptoacetyltriglycine (Tc99m-MAG3), which complex is secreted by the kidneys selectively and approximately equally rapidly as iodo-Hippuran®.

However, the organ specificity of said complexes still leaves something to be desired. In practice this is considered to be a disadvantage, the more so because these compounds are used for function examination. Chemically related compounds having an improved organ specificity are the subject of the recently published European patent application 250013.

In connection with the comparatively short half-life of radionuclides it is often hardly possible or impossible to deliver the ready-to-use labelled product to the user. In such cases it is desirable to place the various reaction components at the user's disposal in a so-called kit. By means of this kit, the user himself can carry out the labelling reaction with the radionuclide in the clinical hospital or laboratory at any desired amount. This is a favorable in particular for preparing technetium-99m-labelled products, because most modern clinical hospitals or laboratories have at their disposal a molybdenum-technetium generator, from which the desired quantity of technitium-99m can very easily be obtained in the form of a pertechnetate solution. It will be obvious that the user must be capable of preparing the technetium-99m-labelled product from the supplied kit with a few simple manipulations, without laborious operations, and by using the facilities which are at his disposition in the clinic. Furthermore, the stability of the labelled product is of great importance. In fact, if the stability is not satisfactory, there is insufficient opportunity to be able to prepare and perform the renal function examination in patients carefully. Moreover, there is a constant risk that if the shelf life is exceeded, as a contaminated composition may be administered to the patient and the results of the examination will no longer be reliable.

It has now been found that the shelf life of technetium-99m complexes described in the European patent applications mentioned hereinbefore are at most a few hours, depending on the complex-forming ligands and the labelling method used. In practice this is often insufficient because it is desired to have a suitable composition available immediately at any instant of the day. Moreover it is advantageous that a radioactive composition need be prepared only once daily. Furthermore the reaction conditions in which the user has to prepare the labelled product from the kit are not very favorable. In fact, in order to prepare the technetium-99m complexes described in the European patent applications, the kit constituents must be heated for at least approximately 5 minutes with the eluate from a molybdenum-technetium generator on a boiling water bath to produce the desired reaction resulting in the formation of the technetium-99m complex. In carrying out this operation, the possibility of accidents in which radioactive material is released are very possible.

It is the object of the present invention to provide a technetium-99m complex suitable for examining the renal function which complex has a high organ specificity and an improved stability, and which is better suitable for the preparation from a kit than the above known complexes.

This object can be achieved by means of a technetium-99m complex according to the invention which satisfies the general formula

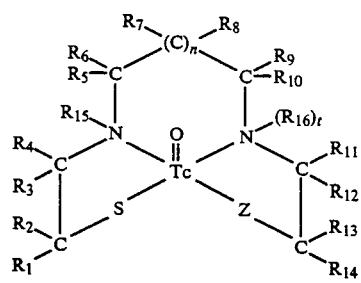 (I)

wherein

Z is a sulphur atom or an amino group of the general formula $R_{17}$—N—$(R_{18})_k$, in which k is 0 or 1 and $R_{17}$ and $R_{18}$ have the same meanings as the symbols $R_1$–$R_{16}$;

each of the symbols $R_1$–$R_{16}$ is individually selected from the group consisting of hydrogen, straight or branched, unsubstituted or substituted alkyl having 1–4 carbon atoms, and ACOOH, wherein A is a straight or branched, unsubstituted or substituted alkyl group having 0–4 carbon atoms; and $R_5$ together with $R_6$ or $R_9$ together with $R_{10}$ additionally may form an oxygen atom;

Tc represents technetium-99m;

t is 0 or 1; and n is 0 or 1;

with the provisos that (a) if $R_{15}$, $R_{16}$, $R_{17}$ and/or $R_{18}$ are/is ACOOH, A is a straight or branched, unsubstituted or substituted alkyl group having 1–4 carbon atoms;

(b) at least one of the symbols $R_1$–$R_{18}$ is ACOOH; and (c) if t is 1, at least two of the symbols $R_1$–$R_{18}$ are ACOOH;

or a pharmaceutically acceptable salt of this compound.

When the above symbols k and/or t are/is 1, there is a coordinative bond between the amino-N and Tc. The cordinative bonds in the above formula I are also denoted by solid lines. The general formula I also includes stereoisomeric structures wherein N—$R_{15}$ has been exchanged with N—$(R_{16})_t$ or S has been exchanged with Z.

If the above symbols represent or include substituted alkyl groups, such substituents are preferably selected from hydroxy groups and acid groups; examples of suitable acid groups are carboxy groups.

Pharmaceutically acceptable salts may be salts with various acids, for example, hydrochloric acid, sulphuric acid, phosphoric acid, perchloric acid or organic acids such as citric acid, tartaric acid, and the like.

The new technetium-99m complexes will usually occur in stereoisomeric configurations which, as will become apparent from the examples, may differ in their biological properties. By starting from the stereochemically most complexes can be prepared having properties which are most favorable for the intended purpose, as will be described in more detail hereinafter.

Chemically related technetium-99m complexes are described in the recently published European patent application 279417. It has been found that these compounds which are destined for brain scintigraphy, are not suitable for examining the renal function.

In view of easy accessibility and biological properties a technetium-99m complex is to be preferred which satisfies the general formula

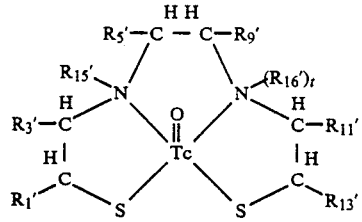 (II)

wherein each of the symbols $R_1'$, $R_3'$, $R_5'$, $R_{11}'$, $R_{13}'$, $R_{15}'$ and $R_{16}'$ is individually selected from the group consisting of hydrogen, methyl and $(CH_2)_1COOH$, wherein q is 0 or 1, Tc represents technetium-99m, and t is 0 or 1, with the provisos that (a) if $R_{15}'$ and/or $R_{16}'$ are/is $(CH_2)_qCOOH$, q is 1, (b) at least one of the symbols $R_1'$, $R_3'$, $R_5'$, $R_9'$, $R_{11}'$, $R_{13}'$, $R_{15}'$ and $R_{16}'$ is $(CH_2)_qCOOH$, (c) at most four of the symbols $R_1'$, $R_3'$, $R_5'$, $R_9'$, $R_{11}'$, $R_{13}'$ and $R_{16}'$ are $(CH_2)_qCOOH$, and (d) if t is 1, at least two of the symbols $R_1'$, $R_3'$, $R_5'$, $R_9'$, $R_{11}'$, $R_{13}'$, $R_{15}'$ and $R_{16}'$ are $(CH_2)_qCOOH$, or a pharmaceutically acceptable salt of this compound.

Examples of technetium-99m complexes according to the invention are the technetium-99m complexes of N,N'-bis(1-carboxy-2-mercaptoethyl)ethylene diamine and N,N'-bis(2-mercaptoethyl)diamino succinic acid, which compounds may occur in the LL-, LD- or DD-configurations, and of N,N'-[bis(2-mercaptoethyl)]-N,N,'-ethylenediamino-diacetic acid.

A technetium-99m complex according the invention is generally used in the form of a composition which is suitable for examining the renal function. In addition to the radioactive complex, such a radiopharmaceutical composition will usually comprise a liquid, pharmaceutically acceptable carrier material, preferably a physiological saline solution. A radiodiagnostic examination can be performed with such a composition by administering the composition to a warm-blooded living being, in particular a primate, in a quantity of 0.1 to 30 mCi, preferably of 0.5 to 10 mCi, per 70 kg of body weight, and by then recording the radioactive radiation emitted by the living being by means of, for example, a gamma camera.

The invention further relates to a method of preparing a technetium-99m complex according to the invention by reacting technetium-99m in the form of a pertechnetate in the presence of a reducing agent and optionally a suitable chelator with a diaminothio compound of the general formula

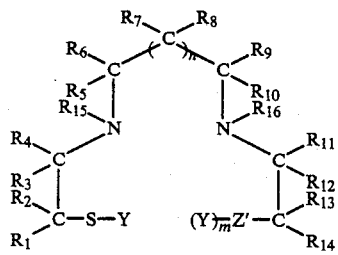

(III)

wherein
the symbols n and $R_1$–$R_{16}$ have the meanings given hereinbefore,
Y is hydrogen atom or a suitable protecting group,
Z' is a sulphur atom or an amino group of the general formula $R_{17}$—N—$R_{18}$, wherein $R_{17}$ and $R_{18}$ also have the above meanings, and
m is 0 or 1, with the provisos that, if Z' is a sulphur atom, m=1 and if Z' is an amino group, M=0.

Examples of suitable protective groups Y for the mercapto group are: acetyl, trifluoroacetyl, hydroxyacetyl, carboxyacetyl, acetamidomethyl, benzoyl, benzyl, benzoylaminomethyl and the like.

The reducing agent serves to reduce the Tc-99m pertechnetate which in a physiological saline solution is eluted from a molybdenum-technetium generator. Suitable reducing agents are, for example, dithionite, formamidine sulphinic acid, diaminomethane disulphinate or suitable metallic reducing agents such as Sn(II), Fe(II), Cu(I), Ti(III) or Sb(III); Sn(II) has proved to be particularly suitable.

For the above-mentioned complex-forming reaction, technetium-99m is presented to the above-mentioned diaminothio compound as a salt or in the form of a chelate bound to comparatively weak chelators; in the latter case the desired technetium-99m complex is formed by ligand exchange. Examples of suitable chelators for the radionuclide are dicarboxylic acids, polycarboxylic acids or hydroxy carboxylic acids, such as oxalic acid, malonic acid, succinic acid, maleic acid, orthophthalic acid, malic acid, lactic acid, tartaric acid, citric acid, ascorbic acid, salicylic acid or derivatives of these acids; phosphorus compounds such as pyrophosphates; or enolates. Citric acid, tartaric acid, ascorbic acid, glucoheptonic acid or a derivative thereof are particularly suitable chelators for this purpose, because it appears that a chelate of technetium-99m with one of these chelators particularly easily undergoes the desired ligand exchange.

It has been found that the above-mentioned complex-forming reaction occurs quanitatively at room temperature i.e. with a radiochemical yield exceeding 98%. So heating of the reaction mixture is not necessary to reach a full conversion to the desired technetium-99m complex.

Since the radiopharmaceutical composition according to the invention can be prepared so easily and simply, the preparation can be carried out particularly readily by the user himself. The invention therefore also relates to a so-called kit as explained hereinbefore, comprising (1) in an optionally dry condition a diaminothio compound of the above general formula III, wherein the symbols have the meanings given hereinbefore and to which optionally an inert, pharmaceutically acceptable carrier and/or auxiliary substances have/has been added, (2) a reducing agent and optionally a chelator, ingredients (1) and (2) being optionally combined, and (3) if desired, instructions for use with a prescription for carrying out the above-described method by reacting ingredients (1) and (2) with technetium-99m in the form of a pertechnetate solution.

Examples of suitable reducing agents and chelators for the above kit have been given hereinbefore. The pertechnetate solution can simply be obtained by the user himself from a molybdenum-technetium generator which is available to him. As indicated hereinbefore, the above-mentioned ingredients (1) and (2) may be combined, provided they are compatible. Such a monocomponent kit, in which the combined ingredients are preferably lyophilized, is excellently suitable to be reacted by the user with the pertechnetate solution in a simple manner.

The constituent (1) of the above kits may be delivered as a solution, for example, in the form of a physiological saline solution, or in some buffer solution, but is preferably present in a dry condition, for example in a lyophilized condition. When used as a component for an injection liquid, it should be sterile, in which, if the constituent is present in a dry condition, the user should use a sterile physiological saline solution as a solvent. If desired, the above-mentioned constituent may be stabilised in a usual manner with suitable stabilisers such as ascorbic acid, gentisic acid or salts of these acids, or it may be provided with other auxiliary means such as fillers, e.g. glucose, lactose, mannitol, inositol, and the like.

The kit according to the invention preferably comprises a diaminodithio compound of the general formula

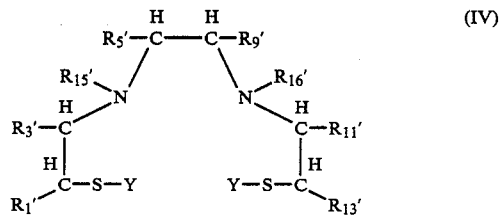

(IV)

wherein the symbols have the meanings given hereinbefore. These complex-forming ligands are readily accessible and can very easily be converted into the desired technetium-99m complexes.

The stereochemical configuration of the technetium-99m complex is determined by the configuration of the starting diaminothio compound of the above general formula III or IV. Different stereoisomers of these diaminothio compounds can be separated from each other by using techniques known for this purpose such as recrystallisation and/or chromatographic methods. If desired, for the separation the stereoisomer mixture may be converted with a stereochemically pure D- or L-isomer of a suitable amine, carboxylic acid, and the like, after which the isomer separation is carried out, succeeded by eliminating the used amine, carboxylic acid, etc. An alternative, also particularly suitable method of preparing stereochemically pure diaminothio compounds, consists in using for the synthesis a starting material which is already stereochemically pure and which is easily available or obtainable as a stereoisomer, and in ensuring that during the synthesis of the intended diaminothiol the stereochemical purity is not lost, i.e. that no racemisation occurs.

The invention will now be described in greater detail with reference to the ensuing specific examples.

EXAMPLE I

Preparation of N,N'-bis(1-carboxy-2-mercaptoethyl)ethylenediamine

The L,L-isomer of the title compound is prepared by reductive dimerisation of L-thiazolidine-4-carboxylic acid under the influence of sodium in liquid ammonia, as described in Blondeau et al in Can. J. Chem. 45 (1), 49–52 (1967). The corresponding D,D-isomer and the meso form (L,L-isomer) are prepared in a corresponding manner from D-thiazolidine-4-carboxylic acid and racemic thiazolidine-4-carboxylic acid, respectively. These thiazolidine carboxylic acids are obtained by reaction of L-, D- or DL-cystein with formaldehyde according to Nagasama et al, J. Med. Chem. 27, 591 (1984).

EXAMPLE II

Labelling of N,N'-bis(carboxy-2-mercaptoethyl)ethylenediamine with technetium-99m 20 mg of [L,L]-N,N'-bis(1-carboxy-2-mercaptoethyl)ethylenediamine are dissolved in 4 ml of 0.5N sodium hydroxide solution while stirring and flushing with nitrogen. The pH of the solution is successively reduced to 10 with 0.5N hydrochloric acid and to 7.5 with 0.1N hydrochloric acid. After diluting with water to 10 ml, vials are dispensed with 0.5 ml solutions under nitrogen or in vacuo. These vials are stored at $-20°$ C. or lyophilized.

For the labelling with technetium-99m the content of a vial is allowed to reach ambient temperature, after which 100 μg of $SnCl_2 2H_2O$, dissolved in 25 μl 0.05N hydrochloric acid, and 1–2 ml of a sodium pertechnetate solution, obtained from a molybdenum-technetium generator and comprising 10–100 mCi Tc-99m-labelled N,N'-bis(1-carboxy-2-mercaptoethyl)ethylenediamine has a radiochemical purity of >98%. The stability of the labelled compound is determined by measuring until 8 hours after preparation the radiochemical purity with TLC or HPLC. The Tc-99m complexes according to the invention prove to be completely stable for at least 8 hours at room temperature. Starting from an optically pure isomer results in a technetium-99m complex of an unambiguous stereoisomer. When a mixture of stereoisomeric diaminodithiols is used as the starting material, the resulting technetium-99m complex may be resolved in its stereoisomers (LL-, DD-, LD-isomer) by means of HPLC. This will be described in example III.

EXAMPLE III

Purification by means of HPLC

The product labelled according to Example II is applied in a quantity of 30 to 150 μl on a column filled with Hypersil ® C8 (3 μm). Gradient elution with 100% 0.0125M phosphate buffer (pH 2.5) to 0.0125M phosphate buffer-ethanol mixture (70:30) yields the desired pure stereoisomers. Detection is performed radiometrically by passing the eluate over a scintillation detector connected to a one-channel analyser and an integrator. After collection of the main fraction, this may be diluted with physiological saline solution for intravenous administration.

EXAMPLE IV

Biodistribution studies in mice

Each time 5 male mice are injected with 0.5 μCi of a Tc-99m-labelled N,N'-bis(1-carboxy-2-mercaptoethyl)ethylenediamine (LL, DD or Dl-isomer) according to the invention. For the validation of the examination, iodo-131-Hippuran ® is used as an internal biological standard. For comparison, 0.5 μCi Tc-99m-mercaptoacetyl triglycin (Tc99m-MAG3) known from European patent application 173424 mentioned hereinbefore, is also tested. After 10 minutes the mice are sacrificed and the radioactivity in the various organs is determined. The accumulated radioactivity in various organs and in urine ("organs") in comparison with that of Tc99m-MAG3 is recorded in the table below.

TABLE

Uptake in organs of mice after 10 minutes as a % of the Tc99m-MAG3 value.

| Organ | LL-isomer | DD-isomer | LD-isomer |
| --- | --- | --- | --- |
| urine | 113,0 | 106,6 | 108,6 |
| kidneys | 37,0 | 41,1 | 37,9 |
| liver | 32,7 | 81,8 | 60,2 |

From the above results it appears that the compounds according to the invention show considerably less liver activity, in which especially the LL-isomer shows very favorable characteristics. Further, from an enhanced activity in the urine and a considerably reduced activity in the kidneys it appears that the plasma clearance and urinary excretion of the compounds according to the invention are very fast in comparison with those of Tc99m-MAG3.

EXAMPLE V

Plasma clearance in a primate

A quantity of 0.5 mCi of Tc-99m N,N'-bis(1-carboxy-2-mercaptoethyl)ethylenediamine, LL- or DD-isomer, is administered intravenously to a male baboon, sedated with Ketalar ® and pentabarbital (I-131 Hippuran ® as an internal biological standard). Through an intra-arterial puncture 0.5 ml-blood samples are taken at regular intervals during 60 minutes. The radioactivity of the samples is determined and the plasma disappearance curves are recorded. The same study is performed in the same animal with Tc99m-MAG3. The plasma clearance is then calculated. For the LL-isomer this value is 119.6% with respect to the plasma clearance of Tc99m-MAG3 and for the DD-isomer 145.1%.

After the injection of 1 mCi the radioactivity is recorded at the region of the kidneys by means of a gamma camera. The maximum kidney accumulation of Tc99m-MAG3, the LL-isomer, the DD-isomer and the LD-isomer of Tc-99m N,N'-bis(1-carboxy-2-mercaptoethyl)ethylenediamine does not differ essentially. For Tc99m-MAG3 the maximum activity in the kidneys is reached after 3.5 minutes, for the isomers according to the invention already after 2.5, 2.5 and 2.0 minutes, respectively. This also clearly indicates a more rapid plasma clearance of the Tc99m-complexes according to the invention compared with the known product.

EXAMPLE VI

Biodistribution studies of Tc-99m [LL]-N,N'-bis(1-carboxy-2-mercaptoethyl)ethylenediamine compared with Tc99m-MAG3 in a human being The above-mentioned labelled diaminodithiol is administered intravenously in a human being in a quantity of 0.5 mCi (I-131 Hippuran ® as an internal biological standard). The radioactivity at the region of the kidneys is recorded by means of gamma camera equipped with a high-sensitive collimator. The maximum renal activity is achieved after 2.5 minutes both for the LL-isomer according to the invention and for Tc99m-LL-isomer than for Tc99m-MAG3.

The renogram obtained with the title compound is approximately identical to the renogram obtained with Tc99m-MAG3 in the same person.

The liver accumulation is determined after 40 minutes. For the tested Tc99m-LL-isomer it amounts to 2.9%, for Tc99m-MAG3 it amounts to 4.0% of the injected dose. From this experiment it appears that for the tested Tc99m complex according to the invention considerably less liver accumulation occurs in the human being than for the known Tc99m-MAG3.

EXAMPLE VII

Renograms of Tc-99m [DD]-N,N'-bis(1-carboxy-2-mercaptoethyl)ethylenediamine compared with Tc99m-MAG3 in human beings In the same manner as indicated in Example VI, the title renograms are obtained in two human volunteers. The maximum renal activity (mean of 2 kidneys) for the title compound is reached after 2.5 and 3.25 minutes for the two volunteers respectively, as compared to 5.0 and 4.0 minutes respectively for Tc99m-MAG3.

We claim:

1. Technetium-99m complex of the general formula

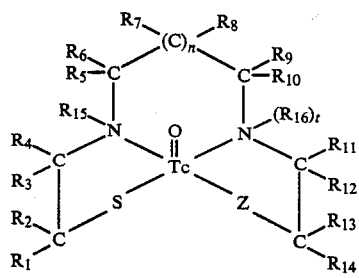

wherein

Z is an amino group of the general formula $R_{17}$—N—$(R_{18})_k$, in which k is 0 or 1 and $R_{17}$ and $R_{18}$ have the same meanings as the symbols $R_1$–$R_{16}$ is individually selected from the group consisting of hydrogen, straight or branched, unsubstituted or substituted alkyl having 1–4 carbon atoms, and ACOOH, wherein A is a straight or branched, unsubstituted or substituted alkyl group having 0–4 carbon atoms; and $R_5$ together with $R_6$ or $R_9$ together with $R_{10}$ additionally may form an oxygen atom;

Tc represents technetium-99m;

t is 0 or 1; and n is 0 or 1;

with the provisos that (a) if at least one of $R_{15}$, $R_{16}$, $R_{17}$ and $R_{18}$ is ACOOH, A is a straight or branched, unsubstituted or substituted alkyl group having 1–4 carbon atoms;

(b) at least one of the symbols $R_1$–$R_{18}$ is ACOOH; and (c) if t is 1, at least two of the symbols $R_1$–$R_{18}$ are ACOOH;

or a pharmaceutically acceptable salt of this compound.

2. A complex as claimed in claim 1 of the general formula

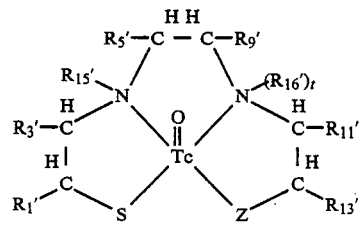

wherein

Z is an amino group of the general formula $R_{17}'$—N—$(R_{18}')_k$, in which k is 0 or 1 and $R_{17}'$ and $R_{18}'$ have the same meanings as the symbols $R_1'$, $R_3'$, $R_5'$, $R_9'$, $R_{11}'$, $R_{13}'$, $R_{15}'$ and $R_{16}'$, each of the symbols $R_1'$, $R_3'$, $R_5'$, $R_9'$, $R_{11}'$, $R_{13}'$, $R_{15}'$ and $R_{16}'$ is individually selected from the group consisting of hydrogen, methyl and $(CH_2)_q$COOH, wherein q is 0 or 1, Tc represents technetium-99m, and t is 0 or 1, with the provisos that (a) if at least one of $R_{15}'$ and $R_{16}'$ is $(CH_2)_q$COOH, q is 1

(b) at least one of the symbols $R_1'$, $R_3'$, $R_5'$, $R_9'$, $R_{11}'$, $R_{13}'$, $R_{15}$ and $R_{16}'$ is $(CH_2)_q$COOH, (c) at most four of the symbols $R_1'$, $R_3'$, $R_5'$, $R_9'$, $R_{11}'$, $R_{13}'$, $R_{15}'$ and $R_{16}'$ are $(CH_2)_q$COOH, and (d) if t is 1, at least two of the symbols $R_1'$, $R_3'$, $R_5'$, $R_9'$, $R_{11}'$, $R_{13}'$, $R_{15}'$ and $R_{16}'$ are $(CH_2)_q$COOH, or a pharmaceutically acceptable salt of this compound.

3. A radiopharmaceutical composition for examining the renal function which, in addition to a liquid, pharmaceutically acceptable carrier material, comprises a technetium-99m complex, characterized in that the composition comprises a complex as claimed in claim 1 or 2 as the technetium-99m complex.

4. A method of performing a renal function examination, characterized in that a composition as claimed in claim 3 is administered to a warm-blooded living being in a quantity of 0.1 to 30 mCi, per 70 kg of body weight, and the radioactive radiation emitted by the living being is then recorded.

5. A method according to claim 4, wherein the quantity of the composition administered is 0.5 to 10 mCi per 70 kg of body weight.

6. Technetium-99m complex of the general formula

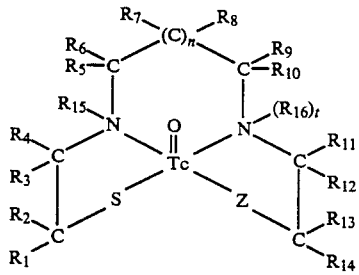

(I)

wherein
- Z is a sulphur atom or an amino group of the general formula $R_{17}-N-(R_{18})_k$,
  in which K is 0 or 1 and $R_{17}$ and $R_{18}$ have the same meanings as the symbols $R_1-R_{16}$;
- each of the symbols $R_1-R_{16}$ is individually selected from the group consisting of hydrogen, straight or branched, unsubstituted or substituted alkyl having 1-4 carbon atoms, and ACOOH, wherein A is a straight or branched, unsubstituted or substituted alkyl group having 0-4 carbon atoms;
- and $R_5$ together with $R_6$ or $R_9$ together with $R_{10}$ additionally may form an oxygen atom;
- Tc represents technetium-99m;
- t is 0 or 1;
- n is 0 or 1;

with the proviso that
- at least two of the symbols $R_1-R_{18}$ are ACOOH, wherein A is a straight or branched unsubstituted or substituted alkyl group having 1-4 carbon atoms, or a pharmaceutically acceptable salt of this compound.

7. A complex as claimed in claim 6, of the general formula

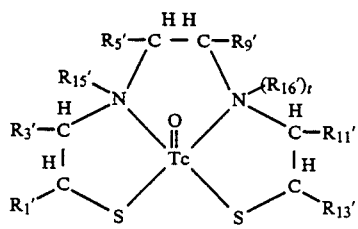

(II)

wherein
- each of the symbols $R_1'$, $R_3'$, $R_5'$, $R_9'$ $R_{11}'$, $R_{13}'$, $R_{15}'$ and $R_{16}'$ is individually selected from the group consisting of hydrogen, methyl and $(CH_2)_qCOOH$, wherein q is 0 or 1,
- Tc represents technetium-99m, and
- t is 0 or 1, with the provisos that
- (a) at least two of the symbols $R_1'$, $R_3'$, $R_5'$, $R_9'$, $R_{11}$, $R_{13}'$, $R_{15}'$ and $R_{16}'$ are $(CH_2)_qCOOH$, wherein q is 1, and
- (b) at most four of the symbols $R_1'$, $R_3'$, $R_5'$, $R_9'$, $R_{11}'$, $R_{13}'$, $R_{15}'$ and $R_{16}'$ are $(CH_2)_qCOOH$, or a pharmaceutically acceptable salt of this compound.

8. A radiopharmaceutical composition for examining the renal function which, in addition to a liquid, pharmaceutically acceptable carrier material, comprises a technetium-99m complex, characterized in that the composition comprises a complex as claimed in claim 6 or 7 as the technetium-99m complex.

9. A method of performing a renal function examination, characterized in that a composition as claimed in claim 8 is administered to a warm-blooded living being in a quantity of 0.1 to 30 mCi per 70 kg of body weight, and the radioactive radiation emitted by the living being is then recorded.

10. A method according to claim 9, wherein the quantity of the composition administered is 0.5 to 10 mCi per 70 kg of body weight.

11. Technetium-99m complex of the general formula

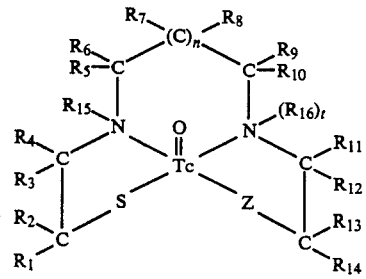

(I)

wherein
- Z is a sulphur atom or an amino group of the general formula $R_{17}-N-(R_{18})_k$,
  in which k is 0 or 1 and $R_{17}$ and $R_{18}$ have the same meanings as the symbols $R_1-R_{16}$;
- each of the symbols $R_1-R_{16}$ is individually selected from the group consisting of hydrogen, straight or branched, unsubstituted or substituted alkyl having 1-4 carbon atoms, and COOH;
- and $R_5$ together with $R_6$ or $R_9$ together with $R_{10}$ additionally may form an oxygen atom;
- Tc represents technetium-99m;
- t is 0 or 1; and
- n is 0 or 1;

with the provisos that
- (a) at least one of the symbols $R_1-R_{18}$ is COOH; and
- (b) if t is 1, at least two of the symbols $R_1-R_{18}$ are COOH, or a pharmaceutically acceptable salt of this compound.

12. A complex as claimed in claim 11 of the general formula

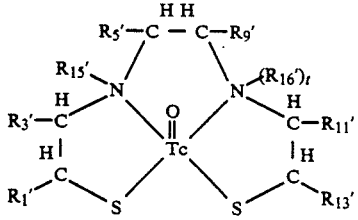

(II)

wherein
- each of the symbols $R_1'$, $R_3'$, $R_5'$, $R_9'$, $R_{11}$, $R_{13}'$, $R_{15}'$ and $R_{16}'$ is individually selected from the group consisting of hydrogen, methyl and COOH,
- Tc represents technetium-99m;
- t is 0 or 1; and
- n is 0 or 1;

with the provisos that
- (a) at least one of the symbols $R_1'$, $R_3'$, $R_5'$, $R_9'$, $R_{11}'$, $R_{13}'$, $R_{15}'$ and $R_{16}'$ is COOH,
- (b) at most four of the symbols $R_1'$, $R_3'$, $R_5'$ $R_9'$, $R_{11}'$, $R_{13}$, $R_{15}'$ and $R_{16}'$ are COOH, and (c) if t is 1, at least two of the symbols $R_1'$, $R_3'$, are COOH, or a pharmaceutically acceptable salt of this compound.

13. A radiopharmaceutical composition for examining the renal function which, in addition to a liquid, pharmaceutically acceptable carrier material, comprises a technetium-99m complex, characterized in that the composition comprises a complex as claimed in claim 11 or 12 as the technetium-99m complex.

14. A method of performing a renal function examination, characterized in that a composition as claimed in claim 13 is administered to a warm-blooded living being in a quantity of 0.1 to 30 mCi per 70 kg of body weight, and the radioactive radiation emitted by the living being is then recorded.

15. A method according to claim 14, wherein the quantity of the composition administered is 0.5 to 10 mCi per 70 kg of body weight.

* * * * *

UNITED STATES PATENT AND TRADEMARK OFFICE
CERTIFICATE OF CORRECTION

PATENT NO. : 4,925,650

DATED : May 15, 1990

INVENTOR(S) : Dennis L. Nosco and Alfons M. Verbruggen

It is certified that error appears in the above-identified patent and that said Letters Patent is hereby corrected as shown below:

Col. 2, line 39,
"as a contaminated" should be --a contaminated--;

Col. 3, line 61,
"stereochemically most complexes" should be
--suitable complex-forming ligands, stereoisomeric technetium--;

Col. 4, line 20, "$(CH_2)_1$" should be --$(CH_2)_q$--;

Col. 4, line 31, "$R_{13}'$ and $R_{16}'$" should be --$R_{13}'$, $R_{15}'$ and $R_{16}'$--;

Col. 7, line 11, "described in Blondeau" should be --described by Blondeau--;

Col. 7, line 37, "$SnCl_2 2H_2O$" should be --$SnCl_2 \cdot 2H_2O$--;

Col. 7, line 40, "Tc-99m-labelled" should be --Tc-99m, are added successively.

The resulting technetium-99m--;

Col. 9, line 56, "$R_1$-$R_{16}$ is" should be --$R_1$-$R_{16}$; each of the symbols $R_1$-$R_{16}$ is--;

UNITED STATES PATENT AND TRADEMARK OFFICE
CERTIFICATE OF CORRECTION

PATENT NO. : 4,925,650

DATED : May 15, 1990

INVENTOR(S) : Dennis L. Nosco and Alfons M. Verbruggen

It is certified that error appears in the above-identified patent and that said Letters Patent is hereby corrected as shown below:

Col. 12, Claim 12, line 63, "n is 0 or 1" should be deleted.

Signed and Sealed this

Seventh Day of April, 1992

Attest:

HARRY F. MANBECK, JR.

*Attesting Officer*    *Commissioner of Patents and Trademarks*